United States Patent
Uckun et al.

(10) Patent No.: US 6,306,897 B1
(45) Date of Patent: Oct. 23, 2001

(54) CALANOLIDES FOR INHIBITING BTK

(75) Inventors: Fatih M. Uckun, White Bear Lake; Elise Sudbeck, St. Paul, both of MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/354,550

(22) Filed: Jul. 15, 1999

Related U.S. Application Data

(60) Provisional application No. 60/126,039, filed on Mar. 19, 1999.

(51) Int. Cl.$^7$ .................................................. A61K 31/35
(52) U.S. Cl. ............................................................ 514/454
(58) Field of Search .............................................. 514/454

(56) References Cited

U.S. PATENT DOCUMENTS

| | | | |
|---|---|---|---|
| 4,559,157 | 12/1985 | Smith et al. | 252/90 |
| 4,608,392 | 8/1986 | Jacquet et al. | 514/841 |
| 4,820,508 | 4/1989 | Wortzman | 424/59 |
| 4,938,949 | 7/1990 | Borch et al. | 624/10 |
| 4,992,478 | 2/1991 | Geria | 514/782 |

FOREIGN PATENT DOCUMENTS

| | | |
|---|---|---|
| WO 94/14789 | 7/1994 | (WO) . |
| WO 96/04263 | 2/1996 | (WO) . |
| WO 99/54286 | 10/1999 | (WO) . |

OTHER PUBLICATIONS

Flavin et al., "Synthesis, Chromatographic Resolution, and Anti–Human Immunodeficiency Virus Activity of (+/−)–Calanolide A and Its Enantiomers", J. Med. Chem. 39, No. 6, pp. 1303–1313, 1996.*
Editor–in–Chief: Jay Stein, Internal Medicine, 4th Edition, Chapters 71 and 72, pp. 699–715, Feb. 15, 1994.*
Jong et al., "An antiplatelet aggregation principle and x–ray structural analysis of cis–khellactone diester from Peucedanum japonicum", Abstract of J. Nat. Prod., 55(10), pp. 1396–1401, 1992.*
Fang et al., "Anticancer action of cube insecticide: correlation for rotenoid constituents between inhibition of NADH:ubiquinone oxidoreductase and induced ornithie decarboxylase activities", Abstract to Proc. Natl. Acad. Sci. U.S.A. 95(7), 1998.*
Bohm, H., "LUDI: Rule–Based Automatic Design of New Substituents for Enzyme Inhibitor Leads", Journal of Computer–Aided Molecular Design, vol. 6, No. 6, pp. 593–606 (Dec. 1992).
Bohm, H., "The Development of a Simple Empirical Scoring Function to Estimate the Binding Constant for a Protein–Ligand Complex of Known Three–Dimensional Structure", Journal of Computer–Aided Molecular Design, vol. 8, No. 3, pp. 243–256 (Jun. 1994).

Flavin, M. et al., "Synthesis, Chromatographic Resolution, and Anti–Human Immunodeficiency Virus Activity of (±)–Calanolide A and Its Enantiomers", J. Med. Chem., vol. 39, No. 6, pp. 1303–1313 (1996).
Hubbard, S., "Crystal Structure of the Activated Insulin Receptor Tyrosine Kinase in Complex with Peptide Substrate and ATP Analog", The EMBO Journal, vol. 16, No. 18, pp. 5572–5581 (Sep. 15, 1997).
Kurosaki, T., "Molecular Mechanisms in B Cell Antigen Receptor Signaling", Curr. Opin. Immunol., vol. 9, No. 3, pp. 309–318 (Jun. 1997).
Mahajan, S. et al., "Rational Design and Synthesis of a Novel Anti–leukemic Agent Targeting Bruton's Tyrosine Kinase (BTK), LFM–A13 [α–Cyano–β–Hydroxy–β–Methyl–N–(2,5–Dibromophenyl)Propenamide]", Journal of Biological Chemistry, vol. 274, No. 14, pp. 9587–9599 (Apr. 2, 1999).
Miyajima, I. et al., "Systemic Anaphylaxis in the Mouse Can Be Mediated Largely through IgG$_1$ and FcγRIII—Assessment of the Cardiopulmonary Changes, Mast Cell Degranulation, and Death Associated with Active or IgE–or IgG$_1$–dependent Passive Anaphylaxis", Journal of Clinical Investigation, vol. 99, No. 5, pp. 901–914 (Mar. 1997).
Mohammadi, M. et al., "Structures of the Tyrosine Kinase Domain of Fibroblast Growth Factor Receptor in Complex with Inhibitors", Science, vol. 276, No. 5314, pp. 955–960 (May 9, 1997).
Ozawa, K. et al., "$Ca^{2+}$–dependent and $Ca^{2+}$–independent Isozymes of Protein Kinase C Mediate Exocytosis in Antigen–stimulated Rat Basophilic RBL–2H3 Cells", Journal of Biological Chemistry, vol. 268, No. 3, pp. 1749–1756 (Jan. 25, 1993).
Rawlings, D. et al., "Mutation of Unique Region of Bruton's Tyrosine Kinase in Immunodeficient XID Mice", Science, vol. 261, pp. 358–361 (Jul. 16, 1993).
Rawlings, D. et al., "Bruton's Tyrosine Kinase is a Key Regulator in B–Cell Development", Immunological Reviews, vol. 138, pp. 105–119 (1994).
Sack, J.S., "Chain—A Crystallographic Modeling Program", J. Mol. Graphics, vol. 6, pp. 224–225 (Dec. 1988).
Sehgal, A. et al., "Application of the Differential Hybridization of Atlas™ Human Expression Arrays Technique in the Identification of Differentially Expressed Genes in Human Glioblastoma Multiforme Tumor Tissue", Journal of Surgical Oncology, vol. 67, Issue 4, pp. 234–241 (1998).

(List continued on next page.)

Primary Examiner—Dwayne C. Jones
(74) Attorney, Agent, or Firm—Merchant & Gould P.C.

(57) ABSTRACT

The invention provides calanolide compounds used as Tec family/BTK inhibitors, methods for their identification and use, and pharmaceutical compositions comprising calanolide Tec family/BTK inhibitors.

29 Claims, 3 Drawing Sheets

OTHER PUBLICATIONS

Sicheri, F. et al., "Crystal Structure of the Src Family Tyrosine Kinase Hck", *Nature*, vol. 385, pp. 602–609 (Feb. 13, 1997).

Tsukada, S. et al., "Deficient Expression of a B Cell Cytoplasmic Tyrosine Kinase in Human X–Linked Agammaglobulinemia", *Cell*, vol. 72, pp. 279–290 (Jan. 29, 1993).

Uckun, F., "Bruton's Tyrosine Kinase (BTK) as a DualFunction Regulator of Apoptosis", *Biochemical Pharmacology*, vol. 56, No. 6, pp. 683–691 (Sep. 15, 1998).

Uckun, F. et al., "BTK as a Mediator of Radiation–Induced Apoptosis in DT–40 Lymphoma B Cells", *Science*, vol. 273, No. 5278, pp. 1096–1100 (Aug. 23, 1996).

Vassilev, A. et al., "Bruton's Tyrosine Kinase as an Inhibitor of the Fas/CD95 Death–inducing Signaling Complex", *Journal of Biological Chemistry*, vol. 274, No. 3, pp. 1646–1656 (Jan. 15, 1999).

Vetrie, D. et al., "The Gene Involved in X–linked Agammaglobulinaemia is a Member of the src Family of Protein-Tyrosine Kinases", *Nature*, vol. 361, No. 6409, pp. 226–233 (Jan. 21, 1993).

Zheng, J. et al., "Å Refined Crystal Structure of the Catalytic Subunit of a cAMP–Dependent Protein Kinase Complexed with MnATP and a Peptide Inhibitor", *Acta Cryst.*, vol. D49, Part 3, pp. 362–365 (May 1, 1993).

* cited by examiner

CALANOLIDES FOR INHIBITING BTK

PRIORITY OF INVENTION

This application claims priority under 35 U.S.C. §119(e) from U.S. Provisional Patent Application No. 60/126,039, filed Mar. 19, 1999.

FIELD OF THE INVENTION

This invention relates to inhibitors of the Tec family tyrosine kinases, and particularly, inhibitors of Bruton's tyrosine kinase (BTK).

BACKGROUND OF THE INVENTION

Bruton's tyrosine kinase (BTK) is a key regulatory enzyme in B-cells, mast cells, and platelets. The ability of B-cells to appropriately respond to antigen has been shown to be dependent on the enzymatic activity of BTK. Similarly, IgE-receptor mediated leukotriene synthesis and release in mast cells is dependent on BTK. BTK is also critical for collagen-induced aggregation of platelets. BTK promotes the survival and drug resistance of leukemia and lymphoma cells. Finally, BTK is required for radiation-induced apoptosis (Ucken et al. 1996, *Science*, 273:1096–1100). Thus, BTK inhibitors have potential for treatment and prevention of various pathologic health conditions due to their activity, for example:

Inhibition of B-cells by BTK Inhibitors: Because of the vital role of BTK in B-cells, BTK inhibitors can be used to inhibit B-cell function and/or to induce B-cell death or apoptosis. Thus, BTK inhibitors are useful in the treatment and inhibition of B-cell mediated autoimmune diseases such as Lupus, B-cell mediated organ transplant rejection (especially xenotransplantation), B-cell mediated drug reactions (anaphalactic shock and the like), B-cell mediated immune-complex disorders, and B-cell mediated resistance to drugs and other treatment agents (neutralizing antibodies to immunotoxins or L-asparaginase in cancer patients, Factor VIII antibodies in hemophiliacs, and the like).

Inhibition of mast cells by BTK inhibitors: Because of the vital role of BTK in mast cells, BTK inhibitors can be used to inhibit mast cell function and/or to induce mast cell death. Thus, BTK inhibitors are useful to treat mast-cell mediated disorders, including allergic and inflammatory disorders (asthma, arthritis, inflammatory bowel disease, and the like).

Inhibition of platelet aggregation by BTK inhibitors: Because of the role of BTK in platelets, BTK inhibitors can be used to inhibit platelet function. Thus, BTK inhibitors are useful to treat or prevent thromboembolic conditions, abnormal platelet aggregation in the context of sepsis, atherosclerosis, vascular injury, and the like.

Inhibition of BTK in leukemia and lymphoma cells: BTK inhibitors can be used to promote apoptosis and reduce drug resistance in leukemia and lymphoma cells.

Inhibition of BTK in B-cell during radiation therapy: BTK inhibitors can be used to prevent undesired immunosuppression during radiation therapy by preventing radiation-induced death of B-cells.

Accordingly, novel inhibitors of BTK and methods for inhibiting BTK are needed for therapeutic use.

SUMMARY OF THE INVENTION

The invention provides calanolide and calanolide analogs or derivatives (hereinafter, collectively referred to as "calanolides") as inhibitors of Tec family tyrosine kinases, and particularly of BTK. The inhibitors of the invention are useful in the treatment of pathologic conditions involving cells expressing Tec family tyrosine kinases, such as T cells (Tec, Itk) and B cells (BTK). Suitable compounds of the invention include compounds of the formula (I). Methods of the invention include the use of such compounds to inhibit Tec family tyrosine kinases, and particularly to inhibit BTK.

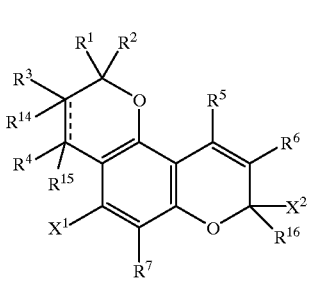

(I)

where:

$R^7$ is —C(=O)$R^8$, —CH(—OH)—$R^8$, or —CH$_2$—$R^8$ wherein $R^8$ is ($C_1$–$C_4$)alkyl, or $R^7$ and $X^1$ together form a fused heterocyclic ring;

$R^1$, $R^2$, $R^3$, $R^4$, $R^5$, $R^6$, $R^{14}$, and $R^{15}$ are the same or different, and are each independently H, OH, SH, CN, halogen, ($C_1$–$C_4$)alkoxy, ($C_1$–$C_4$)alkylthio, ($C_1$–$C_4$) alkyl, ($C_3$–$C_7$)cycloalkyl, aryl, heteroaryl, or NR$^a$R$^b$; wherein R$^a$ and R$^b$ are each independently hydrogen, ($C_1$–$C_4$)alkyl, ($C_3$–$C_7$)cycloalkyl, aryl, or heteroaryl; or R$^a$ and R$^b$ together with the nitrogen to which they are attached form a ring such as pyrrolidino, piperidino, morpholino, or thiomorpholino;

———— is an optional bond;

$X^1$ is a hydrogen bonding group capable of forming a hydrogen bond. Suitable examples of hydrogen bonding groups for use as $X^1$ include OH, SH, NH$_2$, CONH$_2$, COOH. Alternatively, $X^1$ can be a ($C_1$–$C_4$) alkyl, ($C_3$–$C_7$) cycloalkyl, aryl, or heteroaryl, each of which is substituted with one or more hydrogen bonding group, such as OH, SH, NH$_2$, CONH$_2$, COOH. Alternatively, $X^1$ together with $R^7$, forms a fused heterocycle ring; and $X^2$ is a hydrogen bonding group capable of forming a hydrogen bond. Suitable examples of hydrogen bonding groups for use as $X^2$ include =O, =S, =NH, =N—OH, =N—OR$^9$, where R$^9$ is ($C_1$–$C_4$) alkyl or ($C_3$–$C_7$) cycloalkyl. Or $X^2$ can be a ($C_1$–$C_4$) alkyl, ($C_3$–$C_7$) cycloalkyl, aryl, or heteroaryl, each of which is substituted with one or more hydrogen bonding group, such as =O, =S, =NH, =N—OH, =N—OR$^9$, where R$^9$ is ($C_1$–$C_4$) alkyl or ($C_3$–$C_7$) cycloalkyl;

or a pharmaceutically acceptable salt thereof.

Those of skill in the art will recognize that when the optional double bond is present, two groups attached adjacent the double bond, such as $R^{14}$ and $R^{15}$, will not be present.

Some suitable compounds of formula I include compounds of formula II:

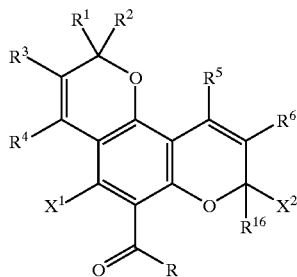

(II)

where:
R is $(C_1-C_4)$alkyl;
$R^1, R^2, R^3, R^4, R^5, R^6$, and $R^{16}$ have the same meanings as given above in formula I;
$X^1$ is OH, SH, $NH_2$, $CONH_2$, COOH; or $X^1$ is $(C_1-C_4)$ alkyl, $(C_3-C_7)$ cycloalkyl, aryl, or heteroaryl, each of which is substituted with one or more of OH, SH, $NH_2$, $CONH_2$, COOH; and
$X^2$ is =O, =S, =NH, =N—OH, =N—$OR^9$, where $R^9$ is $(C_1-C_4)$ alkyl, or $(C_3-C_7)$ cycloalkyl; or $X^2$ is $(C_1-C_4)$ alkyl, $(C_3-C_7)$ cycloalkyl, aryl, or heteroaryl, each of which is substituted with one or more of =O, =S, =NH, =N—OH, =N—$R^9$, where $R^9$ is $(C_1-C_4)$ alkyl or $(C_3-C_7)$ cycloalkyl;
or a pharmaceutically acceptable salt thereof.

Other suitable compounds of formula I include compounds of formula III:

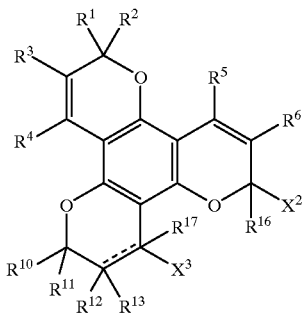

(III)

where:
$R^1, R^2, R^3, R^4, R^5, R^6$ and $X^2$ have the same meanings as given above in formula (I);
$R^{10}, R^{11}, R^{12}, R^{13}, R^{16}$ and $R^{17}$ are the same or different, and are each independently H, OH, SH, halogen, $(C_1-C_4)$ alkoxy, $(C_1-C_4)$ alkylthio, $(C_1-C_4)$ alkyl, $(C_3-C_7)$ cycloalkyl, aryl, heteroaryl or $NR^aR^b$; wherein $R^a$ and $R^b$ are each independently hydrogen, $(C_1-C_4)$ alkyl, $(C_3-C_7)$ cycloalkyl, aryl or heteroaryl; or $R^a$ and $R^b$ together with the nitrogen to which they are attached form a ring such as pyrrolidino, piperidino, morpholino, or thiomorpholino; and
$X^3$ is =O, =S, =NH, =N—OH, =N—$OR^9$, OH, SH, $NH_2$, $CONH_2$ or COOH, where $R^9$ is $(C_1-C_4)$ alkyl or $(C_3-C_7)$ cycloalkyl; and
— — — is an optional bond,
or a pharmaceutically acceptable salt thereof.

Those of skill in the art will recognize that when the optional double bond is present, two groups attached adjacent the double bond, such as $R_{13}$ and $R_{16}$, will not be present.

Examples of specific compounds of the invention include HI-D12, HI-D63, and HI-D86, having the following formulae:

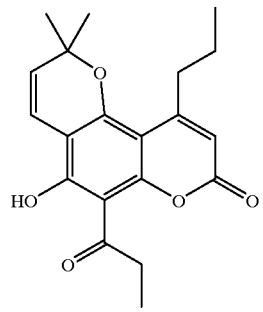

HI-D12

(IV)

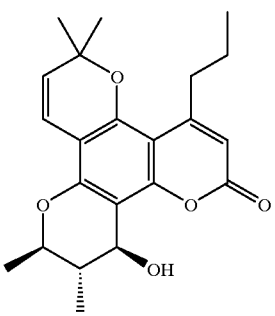

HI-D63

(V)

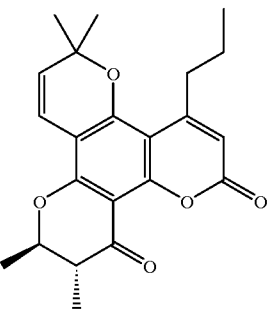

HI-D86

(VI)

The inhibitory compounds of the invention are designed to fit a composite binding pocket model of the BTK catalytic domain. The approximate total volume in catalytic binding sites of BTK is 585 Å$^3$. The compounds of the invention have a molecular volume of less than the volume of the binding pocket (e.g., less than about 585 Å$^3$) and preferably a volume that approaches ⅔ the volume of the pocket, e.g., approximately 400 Å$^3$. Most preferably, the inhibitors of the invention are designed to fill the shape and available space of the binding pocket and to interact favorably with amino acid residues of the pocket for enhanced binding.

The invention provides compositions and methods for inhibiting BTK in a cell by administering to the cell an effective amount of an agent that inhibits or prevents the action of Tec family tyrosine kinases, and particularly of BTK.

The invention also provides therapeutic methods achieved by administering BTK inhibitors, including, treating a pathologic condition regulated by a Tec family TK. Particular therapies include promoting apoptosis, lowering resistance to drug therapy, and other therapies described herein.

The invention provides a BTK inhibitor for use in medical therapy, preferably for use in treating cancer or other BTK regulated disorders, as well as the use of a compound of formula I for the manufacture of a medicament for the treatment of a pathological condition or symptom in a mammal, such as a human, which is regulated by BTK, such as leukemia or lymphoma.

DETAILED DESCRIPTION OF THE INVENTION

Definitions

Figure 1:
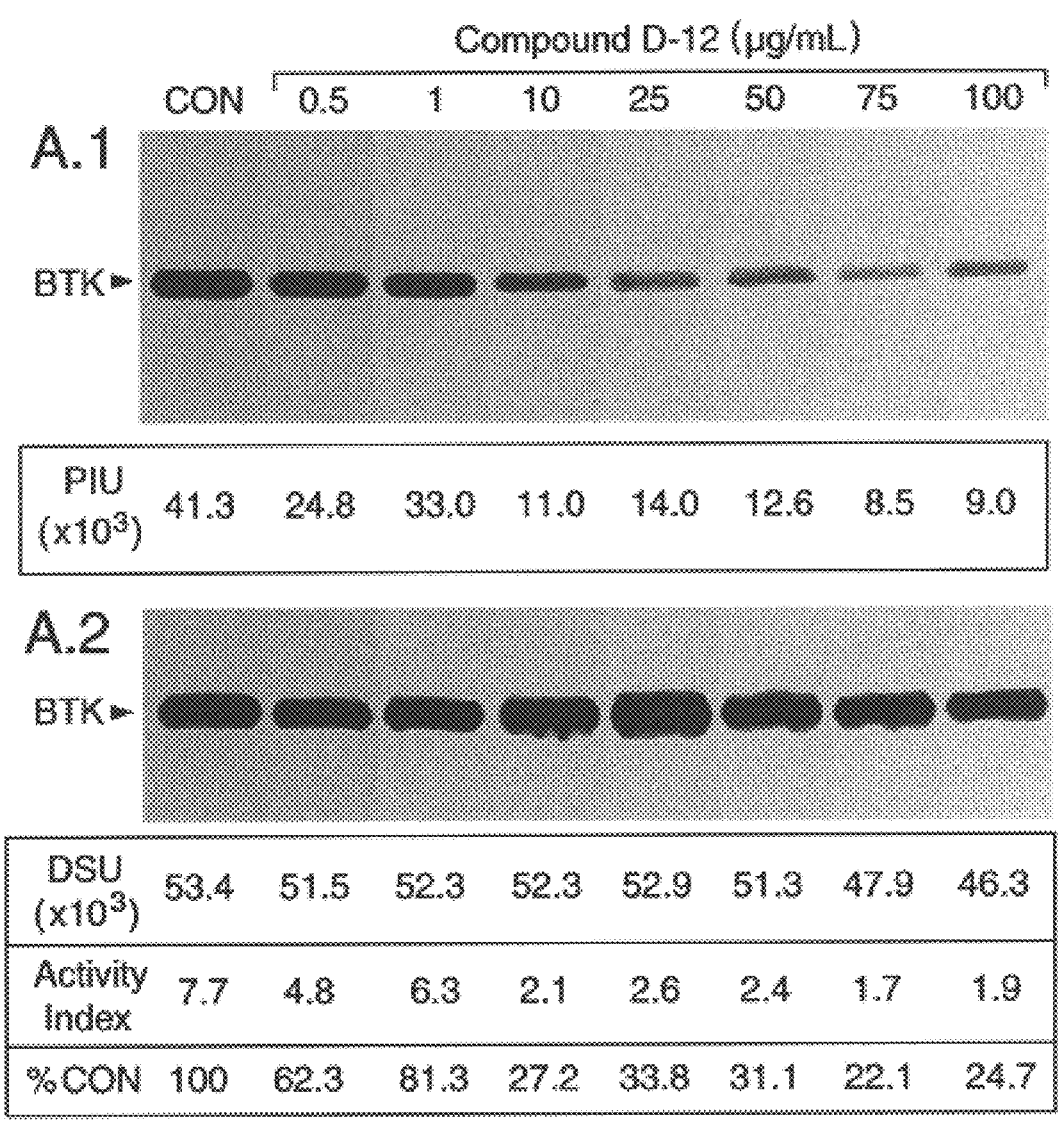
FIG. 1 is a graph showing inhibition of r BTK expressed in a baclovirus vector expression system by HI-D12.

The following definitions are used herein, unless otherwise described: halo is fluoro, chloro, bromo, or iodo. Alkyl, alkoxy, etc. denote both straight and branched groups; but reference to an individual isomer such as "propyl" embraces only the straight chain isomer, a branched chain isomer such as "isopropyl" being specifically referred to. Aryl denotes a phenyl group or a bicyclic or tri-cyclic carbocyclic group having about nine to twelve ring atoms in which at least one ring is aromatic. Heteroaryl encompasses a group attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a group of an ortho-fused bicyclic heterocycle of about eight to ten ring atoms derived therefrom, particularly a benzene derivative or one derived by fusing a propylene, trimethylene, or tetramethylene group thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine BTK inhibiting activity using the standard assays described herein, or using other similar assays which are well known in the art.

Specific and preferred values listed below for substituents and ranges, are for illustration only; they do not exclude other defined values or other values within defined ranges for the radicals and substituents Specifically, $(C_1-C_4)$alkyl can be methyl, ethyl, propyl, isopropyl, butyl, iso-butyl, or sec-butyl; $(C_3-C_7)$cycloalkyl can be cyclopropyl, cyclobutyl, cyclopentyl, cyclohexyl, or cycloheptyl; $(C_1-C_4)$alkoxy can be methoxy, ethoxy, propoxy, isopropoxy, butoxy, iso-butoxy, sec-butoxy; $(C_1-C_4)$alkylthio can be methylthio, ethylthio, propylthio, isopropylthio, butylthio, or isobutylthio; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A pyran ring is a a six membered heterocycle including a single hetero atom which is oxygen.

Hydrogen bonding group means a group on a molecule that is capable of forming a hydrogen bond with another molecule. A hydrogen bond is an attractive force or bridge in which the hydrogen atom of one molecule is attracted to unshared electrons of another molecule.

Inhibiting, or inhibition, in the context of inhibiting the activity of Tec family tyrosine kinase, for example, BTK, means a reduction in the ability of the tyrosine kinase to act as a regulatory enzyme.

BTK

Bruton's tyrosine kinase (BTK), a member of the BTK/Tec family of protein tyrosine kinases (PTKs), is a cytoplasmic PTK involved in signal transduction pathways regulating growth and differentiation of B-lineage lymphoid cells (Rawlings, et al., 1994, *Immunol. Rev.* 138, 105–119; Kurosaki, T., 1997, *Curr Opin. Immunol.* 9, 309–318; and Uckun, F. M., 1998, *Biochemical Pharmacology*, 56; 683–691). BTK participates in signal transduction pathways initiated by the binding of a variety of extracellular ligands to their cell surface receptors: following ligation of B cell antigen receptors (BCR), BTK activation by the concerted actions of the PTKs Lyn and Syk (Kurosaki, T., 1997, *Curr Opin. Immunol.* 9, 309–318) is required for induction of phospholipase C-γ2 mediated calcium mobilization (Kurosaki, T., 1997, *Curr Opin. Immunol.* 9, 309–318). Mutations in the human BTK gene are the cause of X-linked agammaglobulinemia (XLA), a male immune deficiency disorder characterized by a lack of mature, immunoglobulin producing, peripheral B cells (Tsukada, et al., 1993, *Cell* 72, 279–290; and Vetrie et al., 1993, *Nature* 361, 226–233). In mice, mutations in the BTK gene have been identified as the cause of murine X-linked immune deficiency (Rawlings, et al., 1993, *Science* 261, 358–361).

BTK has been shown to be an inhibitor of the Fas/APO-1 death inducing signaling complex (DISC) in B-lineage lymphoid cells (Vassilev et al., 1998, *J. Biol. Chem.*, 274, 1646–1656). Additionally, it has presently been determined that BTK prevents ceramide- and vincristine-induced apoptosis. The fate of leukemia/lymphoma cells may reside in the balance between the opposing proapoptotic effects of caspases activated by DISC and an upstream anti-apoptotic regulatory mechanism involving BTK and/or its substrates (Vassilev et al., 1998, *J. Biol. Chem.*, 274, 1646–1656). Inhibitors of BTK are likely to enhance the drug sensitivity of B-lineage (e.g. leukemia/lymphoma) cells. Thus, pharmacological agents with BTK-modulatory activity can be used as chemosensitizing agents for treating BTK-expressing malignancies or diseases caused by proliferation and antibody production of BTK-expressing B-cells, and as B-cell reconstituting agents in humoral immunodeficiencies with decreased numbers or absence of B-cells. Further BTK modulating agents would be useful as immunosuppressive agents for prevention of hyperacute rejection of organs in transplantation, which is directed by B-cells, autoimmune diseases, and conversion of immunity to drugs (e.g. antibodies or biologicals) or blood products (e.g. coagulation factors such as Factor VIII) in patients who develop antibodies to such agents.

Identification of Inhibitors of BTK

The potent and selective BTK inhibitor HI-D12 and other BTK inhibitors were identified using the three-dimensional homology model of the kinase domain desribed in the Examples below. Using this model and the size and contact information it provided, additional BTK inhibitors were designed and tested. Other compounds that interact favorably with the BTK binding pocket can be designed or identified, as well as compounds that will bind selectively to BTK over other related kinases. Tight binding or a good fit in the binding pocket model correlates with potent BTK-inhibitory activity.

The ability of an agent to inhibit the anti-apoptotic effects of BTK can be measured using assays which are known in the art, or using the assays disclosed in the Examples hereinbelow. Thus, using the modeling information and the screens described herein, as well as other information known in the art, one can identify agents that possess BTK inhibiting properties.

Compounds of the Invention

Compounds of the invention are specific BTK inhibitors which bind favorably to the BTK model pocket described in the examples below, and have potent BTK inhibitory activity as measured by one or more kinase activity assays, for example, in vitro assay utilizing recombinant BTK. Such assays are described more fully in the Examples. The compounds of the invention are designed to fit a composite binding pocket model of the BTK domain, having a molecular volume of less than the volume of the binding pocket (e.g., less than about 585 Å$^3$) and preferably a volume that approaches ⅔ the volume of the pocket, e.g., approximately 400 Å$^3$. Most preferably, the inhibitors of the invention are designed to fill the space of the binding pocket and to interact favorably with residues of the pocket for enhanced binding. Compounds of the invention include compounds of formula I:

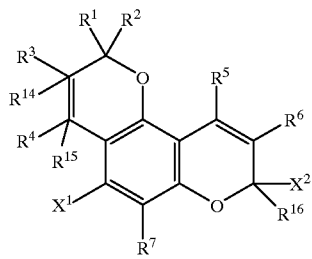

(I)

where:

$R^7$ is —C(=O)$R^8$, —CH(—OH)—$R^8$, or —CH$_2$—$R^8$ wherein $R^8$ is (C$_1$–C$_4$) alkyl, or $R^7$ and $X^1$ together form a fused heterocyclic ring; preferably $X^1$ is O and $R^7$ and $X^1$ together form a substituted or unsubstituted fused pyran ring;

$R^1$, $R^2$, $R^3$, $R^4$, $R^5$, $R^6$, $R^{14}$, $R^{15}$, and $R^{16}$ are the same or different, and are each independently H, OH, SH, CN, halogen, (C$_1$–C$_4$) alkoxy, (C$_1$–C$_4$) alkylthio, (C$_1$–C$_4$) alkyl, (C$_3$–C$_7$) cycloalkyl, aryl, heteroaryl, or NR$^a$R$^b$; wherein R$_a$ and R$^b$ are each independently hydrogen, (C$_1$–C$_4$)alkyl, (C$_3$–C$_7$)cycloalkyl, aryl, or heteroaryl; or R$^a$ and R$^b$ together with the nitrogen to which they are attached form a ring such as pyrrolidino, piperidino, morpholino, or thiomorpholino;

– – – – is an optional bond;

$X^1$ is a hydrogen bonding group capable of forming a hydrogen bond. Preferably, $X^1$ is a hydrogen bonding group capable of forming a hydrogen bond with an amino acid in a catalytic binding cite of a Tec family tyrosine kinase. Suitable examples of hydrogen bonding groups for use as $X^1$ include OH, SH, NH$_2$, CONH$_2$, COOH. Alternatively, $X^1$ can be a (C$_1$–C$_4$) alkyl, (C$_3$–C$_7$) cycloalkyl, aryl, or heteroaryl, each of which is substituted with one or more hydrogen bonding group, such as OH, SH, NH$_2$, CONH$_2$, COOH. In a further embodiment, $X^1$ and $R^7$ together form a fused heterocycle ring; preferably, $X^1$ is O, and $R^7$ and $X^1$ together form a substituted or unsubstituted fused pyran ring; and $X^2$ is a hydrogen bonding group. Preferably, $X^2$ is a hydrogen bonding group capable of forming a hydrogen bond with an amino acid in a catalytic binding site of a Tec family tyrosine kinase. Suitable examples of hydrogen bonding groups for use as $X^2$ include =O, =S, =NH, =N—OH, =N—OR$^9$, where R$^9$ is (C$_1$–C$_4$) alkyl or (C$_3$–C$_7$) cycloalkyl. Alternatively, $X^2$ can be a (C$_1$–C$_4$) alkyl, (C$_3$–C$_7$) cycloalkyl, aryl, or heteroaryl, each of which is substituted with one or more of the hydrogen bonding groups, such as =O, =S, =NH, =N—OH, =N—OR$^9$, where R$^9$ is (C$_1$–C$_4$) alkyl or (C$_3$–C$_7$) cycloalkyl;

or a pharmaceutically acceptable salt thereof.

Those of skill in the art will recognize that when the optional double bond is present, two groups attached adjacent the double bond, such as $R^{14}$ and $R^{15}$, will not be present.

Suitable compounds of formula I include compounds of formulae II and III:

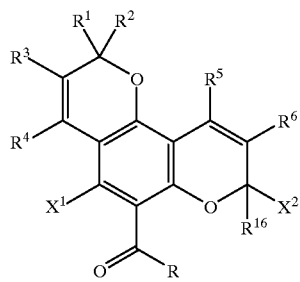

(II)

where:

R is (C$_1$–C$_4$) alkyl;

$R^1$, $R^2$, $R^3$, $R^4$, $R^5$, $R^6$, and $R^{16}$ have the same meanings as given above in formula I.

$X^1$ is OH, SH, NH$_2$, CONH$_2$, COOH, or $X^1$ is (C$_1$–C$_4$) alkyl, (C$_3$–C$_7$) cycloalkyl, aryl, or heteroaryl, each of which is substituted with one or more of OH, SH, NH$_2$,CONH$_2$, COOH;

$X^2$ is =O, =S, =NH, =N—OH, =N—OR$^9$, where R$^9$is (C$_1$–C$_4$) alkyl, or (C$_3$–C$_7$) cycloalkyl. Or $X^2$ is (C$_1$–C$_4$) alkyl, (C$_3$–C$_7$) cycloalkyl, aryl, or heteroaryl, each of which is substituted with one or more hydrogen bonding group, such as =O, =S, =NH, =N—OH, =N—R$^9$, where R$^9$ is (C$_1$–C$_4$) alkyl or (C$_3$–C$_7$) cycloalkyl.

or a pharmaceutically acceptable salt thereof.

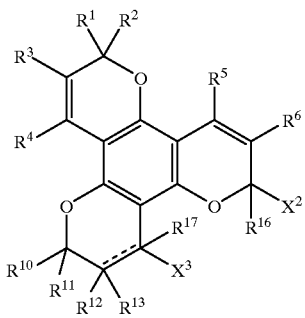

(III)

where:

R$^1$, R$^2$, R$^3$, R$^4$, R$^5$, R$^6$ and X$^2$ have the same meanings as given above in formula (I);

R$^{10}$, R$^{11}$, R$^{12}$, R$^{13}$, R$^{16}$, and R$^{17}$ are the same or different, and are each independently H, OH, SH, CN, halogen, (C$_1$–C$_4$) alkoxy, (C$_1$–C$_4$) alkylthio, (C$_1$–C$_4$) alkyl, (C$_3$–C$_7$) cycloalkyl, aryl, heteroaryl or NR$^a$R$^b$; wherein R$^a$ and R$^b$ are each independently hydrogen, (C$_1$–C$_4$) alkyl, (C$_3$–C$_7$) cycloalkyl, aryl or heteroaryl; or R$^a$ and R$^b$ together with the nitrogen to which they are attached form a ring such as pyrrolidino, piperidino, morpholino, or thiomorpholino;

— — — is an optional bond; and

X$^3$ is =O, =S, =NH, =N—OH, =N—OR$^9$, OH, SH, NH$_2$, CONH$_2$ or COOH, where R$^9$ is (C$_1$–C$_4$) alkyl or (C$_3$–C$_7$) cycloalkyl;

or a pharmaceutically acceptable salt thereof.

Those of skill in the art will recognize that when the optional double bond is present, two groups attached adjacent the double bond, such as R$^{13}$ and R$^{17}$, will not be present.

Preferred compounds for formulae II and III are those wherein

R is ethyl;

R$^1$ is methyl;

R$^2$ is methyl;

R$^3$ is hydrogen;

R$^4$ is hydrogen;

R$^5$ is propyl;

R$^6$ is hydrogen;

R$^{10}$ is hydrogen;

R$^{11}$ is hydrogen;

R$^{12}$ is hydrogen;

R$^{13}$ is hydrogen;

X$^1$ is hydroxy;

X$^2$ is =O; and

X$^3$ is hydroxy or =O.

One specific example of a compound of formula I, HI-D 12, is shown below:

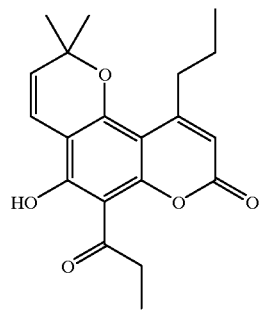

(IV)

HI-D12

Specific examples of compounds of formula II are HI-D63 and HI-D86, shown below:

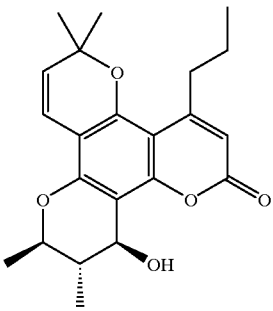

(V)

HI-D63

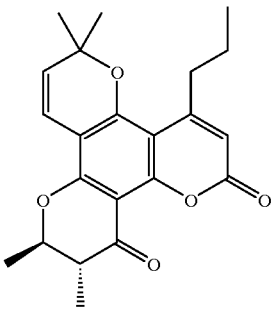

(VI)

HI-D86

Methods of Use

The inhibitors of the invention are useful to inhibit Tec family tyrosine kinase activity in cells expressing this kinase, such as B-cells, mast cells, cancer cells (of B-cell lineage) and platelet cells.

B-cells and B-cell precursors expressing BTK have been implicated in the pathology of a number of diseases and conditions including B-cell malignancies (acute lymphoblastic leukemia, chronic lymphocitic leukemia, non-Hodgkin's lymphoma, EBV lymphomia, and myeloma, and the like), other cancers such as breast cancer, B-cell lymphoproliferative disorders/autoimmune diseases (lupus, Crohn's disease, and chronic or graft-versus-host disease, and the like), mast cell disorders (e.g. allergies, and anaphylactic shock, and the like), and conditions that relate to improper platelet aggregation, and rejection of xenotransplants (e.g. pig to human heart transplants). Inhibition of BTK according to the method of the invention is thus therapeutically useful.

Additionally, the selective BTK inhibitors of the invention can be used to identify other diseases wherein BTK plays a role, and particularly to identify gene expression that is modulated by BTK. This can be done using techniques that are known in the art, for example, using gene profiling techniques similar to those described by A. Sehgal et al. *Journal of Surgical Oncology*, 1998, 67, 234–241. Incubating cells in the presence or absence of a BTK inhibitor followed by profiling of gene expression in the cells is useful to identify BTK-regulated gene expression. Materials useful for profiling gene expression using Atlas cDNA membranes can be obtained from CLONTECH Laboratories, Inc. 1020 East Meadow Circle, Palo Alto, Calif. 94303. cDNA microarrays can also be ordered from commercial sources or be custom made.

Using such materials according to the manufacturer's instructions, it has also been discovered that BTK modulates the expression of specific genes, for example, MAPKAP kinase and c-myc oncogene. This activity suggests that BTK may be implicated in the pathology of all forms of cancer.

BTK is a member of the Tec family of tyrosine kinases, some of which are expressed, for example, in T-cells. The BTK inhibitors of the invention are also useful to inhibit the activity of other members of the Tec kinase family. Thus, BTK inhibitors (including compounds of formula I and II as described herein) can be used to treat disorders wherein the inhibition or prevention of the activity of a Tec family kinase, including BTK, is indicated. It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Conjugation to a Targeting Moiety

The compounds of the invention can be targeted for specific delivery to the cell type to be treated by conjugation of the BTK inhibitor to a targeting moiety. Targeting moieties useful for conjugation to BTK inhibitors include antibodies, cytokines, and receptor ligands that are specific to the cell to be treated.

The term "conjugate" means a complex formed as a composite between two or more molecules.

The phrase "targeting moiety" means a molecule which serves to deliver the compound of the invention to a specific site for the desired activity. Targeting moieties include, for example, molecules that bind molecules present on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

Particularly useful targeting moieties for targeting the BTK-inhibitory compounds of the invention to cells for therapeutic activity include those ligands present on Tec kinase expressing cells. For example, antigens present on B-cells and B-lineage cancer cells, such as CD19 can be targeted with anti-CD19 antibodies such as B43. Antibody fragments, including single chain fragments can be used. Natural ligands for the surface antigens such as CD19 can also be used. Tec kinase expressing T cells can be targeted, for example to the CD7 antigen with anti-CD7 antibodies such as TXU. Mast cells can be targeted via the CD48 antigen with anti-CD48 antibodies. These and other cell surface antigen antibodies are commercially available, for example, from Pharmingen.

Cytokines are also useful targeting moieties. T cells can be targeted with IL2 and IL7; B cells can be targeted with IL4; mast cells can be targeted with C-KIT, MGF, GMCSF, and IL3. Cancer cells expressing a Tec family kinase can be targeted, for example, with EGF and IGF. Other known ligand-receptor pairs can also be used to target the compounds of the invention to cells.

Compounds as Salts

In cases where an agent ("compound") is sufficiently basic or acidic to form stable nontoxic acid or base salts, administration of the compounds as salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Prodrug Derivatives

The compounds of the invention may have attached thereto functional groups to provide a prodrug derivative. The prodrug derivative facilitates use of the drug in the body, for example, by facilitating entry into cells. The term "prodrug moiety" means a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolyzed in vivo.

Pharmaceutical Formulations

A compound can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salt can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active compound which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active compound plus any additional desired ingredient present in the previously sterile-filtered solutions.

For topical administration, the compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active compound per unit dosage form.

Ideally, the active compound should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As disclosed in copending PCT Patent Application Number PCT/US99/08559, which is hereby incorporated by reference for all purposes, it has been discovered that BTK inhibitors are useful as chemosensitizing agents, and thus, are useful to increase the sensitivity of a cancer cell to other chemotherapeutic agents that promote apoptosis. As such, BTK inhibitors can conveniently be administered in combination with other chemotherapeutic agents. Additionally, the pharmaceutical compositions of the present invention that comprise an agent that inhibits BTK, can also further comprise one or more other chemotherapeutic agents that promote apoptosis.

The invention will now be illustrated by the following non-limiting Examples.

EXAMPLES

Example 1

Synthesis of Specific Calanolides and Calanolide Derivatives

Calanolide compounds HI-D12, HI-D86, and HI-D63 were prepared according to the methods described in Flavin et al., 1996 *J. Med. Chemm* 39:1303–1313.

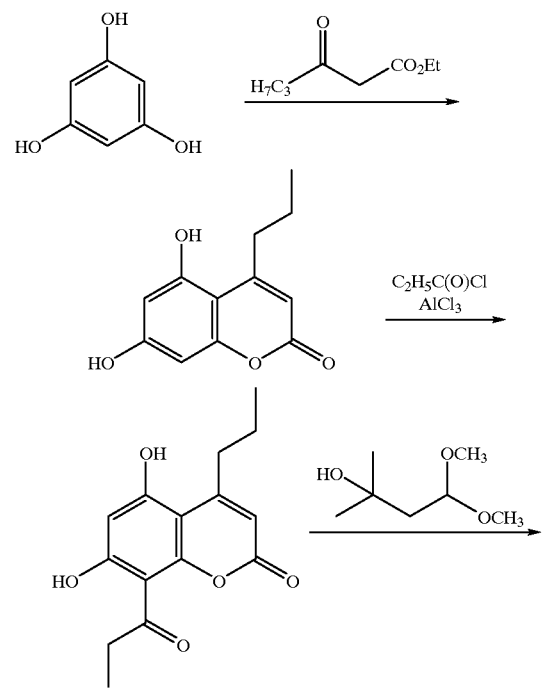

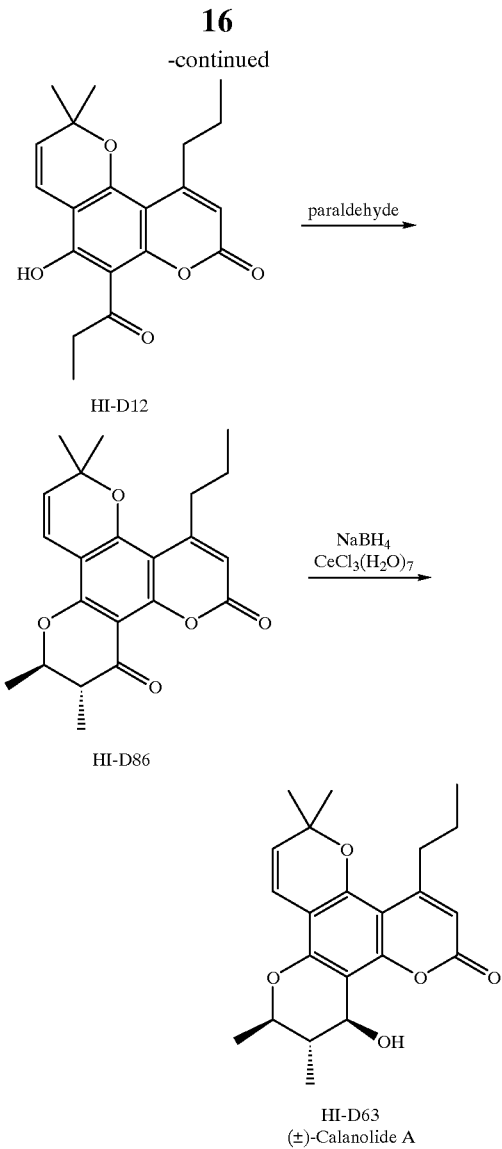

Synthetic Procedures

Calanolide A and its intermediates were synthesized according to literature procedures with a few modifications using the method shown in Scheme 1. The starting material, 5,7-dihydroxy-4-propyl coumarin, was synthesized by the acid condensation of phloroglucinol and ethyl butyrylacetate. Friedel-Crafts acylation, using either the acid chloride or anhydride gave the 8-acyl coumarin derivatives. In general, the anhydride was used, if available, as it gave better yields. The yield was also improved by adding nitrobenzene to the reaction mixture in the Friedel-Crafts acylation to increase solubilization of the coumarin derivatives. Reactions were carried out under nitrogen unless otherwise stated.

Synthesis of 6,6 Dimethyl-9-hydroxy-10-propionyl-4-propyl-2H,6H-benzo[1,2-b:3,4-b']dipyran-2-one (HI-D12)

5,7-Dihydroxy-8-propionyl-4-propylcoumarin (2.60 g) and 4,4 dimethoxy-2-methylbutan-2-ol (5.6 g) were combined in dry pyridine (6.5 mL). The mixture was refluxed for 3 days under nitrogen balloon. The solvent was removed in vacuo and the resulting solid dissolved in ethyl acetate. The solution was then washed three times with 1N HCl and three times with brine. The resulting washes were then combined and extracted once with ethyl acetate. The organic extracts were combined, dried with $Na_2SO_4$, and the solvent was removed. The crude product was obtained from column chromatography eluting with 1:3 ethyl acetate/hexanes.

Synthesis of 12-Oxocalanolide A (HI-D86)

Paraldehyde (3 mL, 22.5 mmol) was added to a solution of HI-D12 (350 mg, 1 mmol), and pyridinium tosylate (PPTS) (250 mg, 1 mmol) in 1,2-dichloroethane (2 mL) (13). The resulting mixture was refluxed for 7 hours. An additional equivalent of PPTS, 1 mL of paraldehyde and 1 mL of triflouroacetic acid were added to the solution and refluxed overnight. The reaction mixture was neutralized with careful addition of a saturated solution of sodium hydrogen carbonate. The mixture was extracted with ethyl acetate, dried with $Na_2SO_4$ and the solvent removed in vacuo. The product, 100 mg (27% yield), was isolated from column chromatography with 1:2 ethyl acetate/Hexanes.

Synthesis of (±)-Calanolide A (HI-D63)

HI-D86 (150 mg) and $CeCl_3(H_2O)_7$ (155 mg) were stirred in ethanol (5 ml). In one portion, $NaBH_4$ (30 mg) was added during stirring. After 30 minutes the reaction was quenched with addition of water, extracted with three portions of ethyl acetate and dried with $Na_2SO_4$. The organic layer was concentrated and purified by column chromatography eluting with 1:6 ethyl acetate/hexanes.

Characterization Methods and Data

Characterization Methods

Nuclear magnetic resonance spectra ($^1$H NMR, $^{13}$C NMR) were determined using a Varian (Palo Alto, Calif.) 300 MHz spectrometer. Chemical shifts are given in ppm downfield from tetramethylsilane as the internal standard. UV spectra were obtained on a Beckman (Fullerton, Calif.) DU 7400 UV/Vis spectrometer. Infrared spectra were recorded using a Nicolet (Madison, Wis.) FT-IR Protege 460 spectrometer. GC/MS spectral analysis were obtained using a Finnigan (San Jose, Calif.) MAT 95 instrument and a Hewlett Packard (Palo Alto, Calif.) 6890GC machine coupled to a HP5973 mass spectra detector. Other samples were also analyzed using a Hewlett-Packard Matrix Assisted Laser Desorption Ionization Time of Flight (MALDI-TOF) mass spectrometer, with cyano-hydroxy cinnamic acid as the matrix. Analytical TLC was performed on aluminum-backed plates with E. Merck Silica Gel-60 F-254. Flash column chromatography was performed on silica gel-60 (230–400 mesh). Melting points were determined with a Fisher-Johns apparatus and are uncorrected. All chemical reagents and anhydrous solvents were purchased from Aldrich Chemical Company (Milwaukee, Wis.) and were used without further purification.

Characterization Data 6,6 Dimethyl-9-hydroxy-10-propionyl-4-propyl-2H, 6H-benzo[1,2-b:3,4-b']dipyran-2-one (HI-D12)

$^1$H NMR (300 MHz, CDCl$_3$) d 1.01 (t, J=7.5 Hz, 3H), 1.19 (t, J=7.5 Hz, 3H), 1.50 (s, 6H), 1.62 (m, 2H), 2.87 (m, 2H), 3.30 (q, J=7.5 Hz, 2H), 5.54 (d, J=10.0 Hz, 1H), 5.96 (s, 1H), 6.69 (d, J=10.0 Hz, 1H); $^{13}$C NMR (75 MHz, CDCl$_3$)Λ 206.68, 162.79, 159.25, 158.39, 157.33, 156.41, 126.30, 115.84, 110.36, 105.89, 104.14, 102.64, 79.59, 38.98, 38.30, 28.21, 23.28, 13.98, 8.42; IR 3444, 2976, 1740, 1601, 1389, 1198 cm$^{-1}$; GC/MS m/z 342 (M), 327 (M–CH$_3$).

10,11-trans-Dihydro-6,6,10,11-tetramethyl-4-propyl-2H,6H,12H-benzo[2-b:3,4-b':5,6-b"]tripyran-2,12-dione (HI-D86)

$^1$H NMR (300 MHz CDCl$_3$) d 1.00 (t, J=7.5 Hz, 3H), 1.19 (d, J=7.0 Hz, 3H), 1.49 (s, 3H), 1.51 (d, J=6.5 Hz, 3H), 1.53 (s, 3H), 1.61 (m, 2H), 2.52 (dq, J=11.0, 7.0 Hz), 2.85 (m, 2H), 4.26 (dq, J=11.0, 6.5 Hz, 1H), 5.57 (d, J=10.0 Hz, 1H), 6.01 (s, 1H), 6.63 (d, J=10.0 Hz, 1H); $^{13}$C NMR (75 MHz, CDCl$_3$) Λ189.77, 159.57, 158.91, 156.95, 155.78, 155.35, 126.90, 115.73, 111.92, 105.40, 104.33, 103.41, 79.51, 79.18, 47.26, 38.75, 28.31, 27.99, 23.19, 19.64, 13.96, 10.52; IR 2964, 1738, 1686, 1556, 1338 cm$^{-1}$; MS (MALDI-TOF) m/z 369 (M+1), 391 (M+Na).

(±)-Calanolide A (HI-D63)

$^1$H NMR (300MHz CDCl$_3$) d 1.01 (t, J=7.5 Hz, 3H), 1.13 (d, J=6.5 Hz, 3H), 1.43 (s, 3H), 1.44 (d, J=6.5 Hz, 3H), 1.49 (s, 3H), ), 1.63 (m, 2H), 1.90 (m, 1H), 2.87 (m, 2H), 3.50 (bs, 1H), ), 3.90 (dq, J=9.0, 6.5 Hz, 1H), 4.70 (d, J=8.0 Hz, 1H), 5.52 (d, J=10.0 Hz, 1H), 5.92 (s, 1H), 6.60 (d, J=10.0 Hz, 1H); $^{13}$C NMR (75 MHz, CDCl$_3$) Λ160.29, 158.67, 154.35, 152.95, 150.97, 126.83, 116.18, 110.04, 106.29, 106.24, 103.94, 77.42, 77.00, 67.00, 40.42, 38.63, 28.02, 27.38, 23.26, 18.96, 15.11, 14.01; IR 3437, 2980, 1701, 1581, 1113 cm$^{-1}$; GC/MS m/z 371 (M+1), 353 (M–OH).

Crystal Structure of HI-D12 (FIG. 2)

Thin yellow plate shaped crystals of HID12 were grown from ethyl acetate 2-propanol by slow at room temperature. A crystal was mounted on a glass fiber using epoxy and X-ray diffraction data (1=0.71073 Å) were collected at room temperature using a SMART CCD X-ray detector (Bruker Analytical X-ray Systems, Madison, Wis.). Structure solution and refinement was performed using the SHELXTL suite of programs (Bruker Analytical X-ray Systems, Madison, Wis.) using full-matrix least-squares refinement on F$^2$, and reflections were corrected for absorption using semi-empirical psi-scan data. All nonhydrogen atoms were refined anisotropically. Hydrogen atoms were placed at ideal positions and refined as riding atoms with relative isotropic displacement parameters. Space group: P2$_1$/n, unit cell: a=6.6444(2) Å, b=22.0556(1) Å, c=11.5899(3) Å, a=90°, b=97.526(1)°, g=90°, Z=4, q range for data collection=1.85 to 25.14° (1=0.71073 Å), total reflections collected=8339, independent reflections=2957 (R$_{int}$=0.0302), data/restraints/parameters=2957/0/231, R1=0.0505 (I>2s(I)), wR2=0.1017, Goodness of Fit on F$^2$=1.051.

Example 2

Inhibition of BTK by Calanolides

The effects of calanolides on the enzymatic activity of the tyrosine kinase BTK in kinase assays was evaluated using recombinant BTK, according to the methods previously reported (Mahajan et al., 1999, *J Biol. Chem.*, 274:9587–9599).

Cell Culture

Sf21 (IPLB-SF21-AE) cells, derived from the ovarian tissue of the fall armyworm *Spodotera frugiperda*, were obtained from Invitrogen and maintained at 26–28° C. in Grace's insect cell medium supplemented with 10% FBS and 1.0% antibiotic/antimycotic (GIBCO-BRL). Stock cells were maintained in suspension at 0.2–1.6×10$^6$/ml in 600 ml total culture volume in 1 L Bellco spinner flasks at 60–90 rpm. Cell viability was maintained at 95–100% as determined by trypan blue dye exclusion.

BTK Expressing Baculovirus

To construct the recombinant baculovirus containing the murine BTK gene, the gene encoding BTK was excised from pBluescript SKII+ vector (Stratagene) by digestion with BamHI. This fragment was then ligated into pFastBac1 (Gibco-BRL). The resulting vector, pFastBac1-BTK, was used to generate the recombinant baculovirus by site-specific transposition in *E. coli* DH10Bac cells (Gibco-BRL), which harbor a baculovirus shuttle vector (bacmid), bMON14272. The resulting recombinant bacmid DNA was introduced into insect cells by transfection with the standard liposome-mediated method using Cellfectin reagent (Gibco-BRL). Four days later, transfection supernatants were harvested for subsequent plaque purification and analyzed.

Kinase Assay

Immunoprecipitations, immune-complex protein kinase assays, and immunoblotting using the ECL chemiluminescence detection system (Amersham Life Sciences) were conducted as described previously (Mahajan et al., 1999, *J. Biol. Chem.*, 274:9587–9599). Following electrophoresis, kinase gels were dried onto Whatman 3M filter paper and subjected to phosphoimaging on a Molecular Imager (Bio-Rad, Hercules, Calif.) as well as autoradiography on film. Similarly, all chemiluminescent BTK Western blots were subjected to three dimesional densitometric scanning using the Molecular Imager and Imaging Densitometer using the Molecular Analyst/Macontosh version 2.1 software following the specifications of the manufacturer (Bio-Rad). For each drug concentration, a BTK kinase activity index was determined by comparing the ratios of the kinase activity in phosphorimager units (PIU) and density of the protein bands in densitometric scanning units (DSU) to those of the baseline sample and using the formula: Activity Index=[PIU of kinase band/DSU of BTK protein band]$_{test\ sample}$:[PIU of kinase band/DSU of BTK protein band]$_{baseline\ control\ sample}$. Horse radish peroxidase-conjugated sheep anti-mouse, donkey anti-rabbit secondary antibodies and ECL reagents were purchased from Amersham (Oakbrook, Ill.).

Results

The calanolides, HI-D12, HI-D63, and HI-D86 inhibited recombinant BTK expressed in a baculovirus vector expression system in a concentration-dependent fashion. Compound HI-D12 inhibited BTK expression with an IC$_{50}$ value of 29 μM (Table 1). The inhibitory activity of calanolides against BTK was specific, since it did not affect the enzymatic activity of other protein tyrosine kinases, including Janus kinases JAK3, SYK, and HCK at concentrations as high as 100 μM. The results of a representative experiment using D-12 are depicted in FIG. 1.

TABLE 1

| Compound | IC$_{50}$ BTK (μM) |
|---|---|
| HI-D12 | 29 |
| HI-D63 | 130 |
| HI-D86 | 110 |

Example 3

Effect Calanolides on Mast Cell Responses in vitro

Background Information on Leukotrienes

Mast cells participate in allergy and asthma through the release of chemical mediators, including pro-inflammatory leukotrienes after crosslinking of their high affinity surface IgE receptors/Fc&RI. Leukotrienes are a group of inflammatory mediators which arc produced in a multistep process triggered by activation of the 5-lipoxygenase (5-LO) pathway.

First, the monooxygenase activity of 5-LO results in oxygenation of the 20-carbon fatty acid arachidonic acid to form 5-hdroperoxyeicosatetraenoic acid (5-HPETE). Next, the dehydrase activity of 5-LO catalyzes the conversion of 5-HPETE to an unstable epoxide intermediate (LTA$_4$), which is converted by a zinc-dependent cytosolic hydrolase to leukotriene B$_4$ (LTB$_4$) or conjugated by a glutathione S transferase (viz., LTC$_4$ synthase) to glutathione to form the C6 peptide leukotriene C$_4$ (LTC$_4$). LTB$_4$, as a potent chemotactic peptide, initiates a local inflammatory response by recruiting neutrophils and eosinophils. LTC$_4$ is converted to the other C6 peptide leukotrienes LTD$_4$ and LTE$_4$.

The C6 peptide leukotrienes LTC$_4$, LTD$_4$ and LTE$_4$, as potent smooth muscle contractiles and vasoactive factors comprising the slow-reacting substance of anaphylaxis, participate in the pathophysiology of reactive airway disease and asthma by (i) inducing contractions of the airway smooth muscles as well as increasing microvascular permeability and edema formation in the bronchial wall both of which lead to bronchoconstriction, and (ii) stimulating mucus secretion in the airway which can aggrevate the airway obstruction. Furthermore, LTD4 is selectively chemotactic for eosinophils.

Methods

Simulation of Mast Cells

RBL-2H3 cells were sensitized with monoclonal anti-DNP IgE antibody (0.24 mg/ml) for 1 hour at 37° C. in a 48-well tissue culture plate. RBL-2H3 cells were allowed to adhere to the plate, whereas bone marrow mast cells (BMMC) were used in suspension. Unbound IgE was removed by washing the cells with phosphate buffered saline. After washing the BMMC were re-suspended in RPMI-hepes buffer. PIPES-buffered saline containing 1 mM calcium chloride was added to the monolayers of the RBL-2H3 cells.

To study the effects of compound HI-D12, mast cells were incubated with compound HI-D12 at the indicated concentrations or vehicle for 1 hour prior to challenge. The cells were challenged with 20 ng/ml DNP-BSA for 30 minutes at 37° C. The plate was then centrifuged at 200 g for 10 minutes at 4° C. Supernatants were removed and saved. RBL-2H3 cell pellets were washed with phosphate buffered saline and solubilized in PIPES buffered saline containing 0.1% Triton X-100.

Mediator Release Assays

Leukotriene (LT) C$_4$ levels were estimated in cell free supernatants by immunoassay using (LT) C$_4$ ELISA kits obtained from Cayman Company (Ann Arbor, Mich.), according to the manufacturer instructions. β-hexosaminidase release was estimated in cell free supernatants and Triton X-100 solubilized pellets, using the method described in Ozawa et al, 1993, J. Biol. Chem., 268:1749–1756.

Results

Figure 2A:
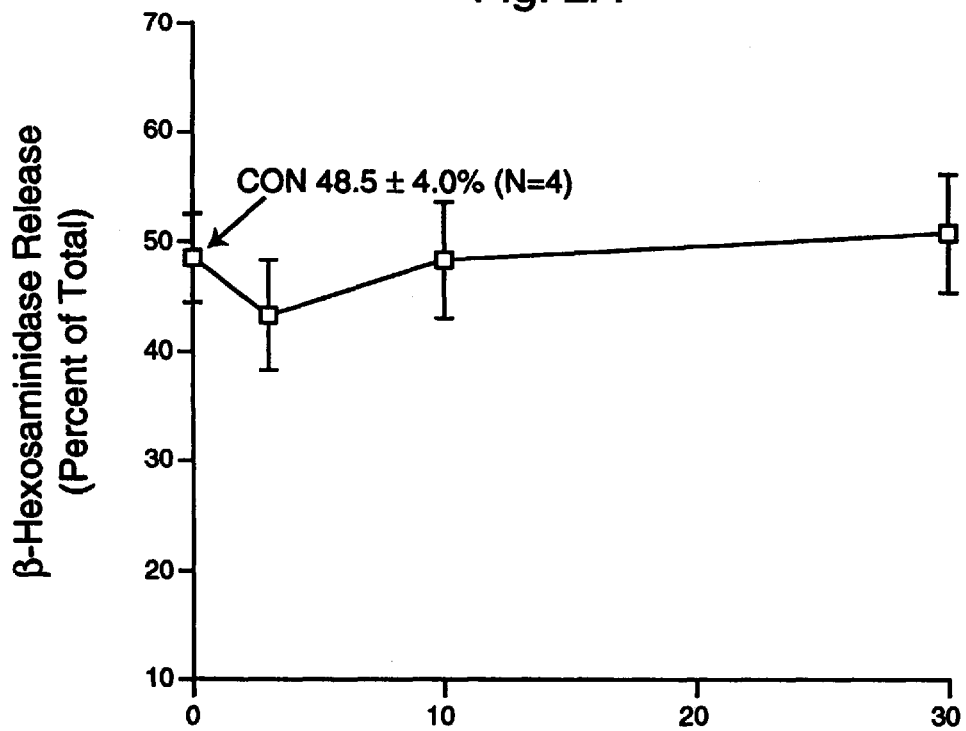
FIG. 2A is a graph showing ∂-hexosaminidase released from RBL-2H3 mast cells incubated with HI-D12.
Figure 2B:
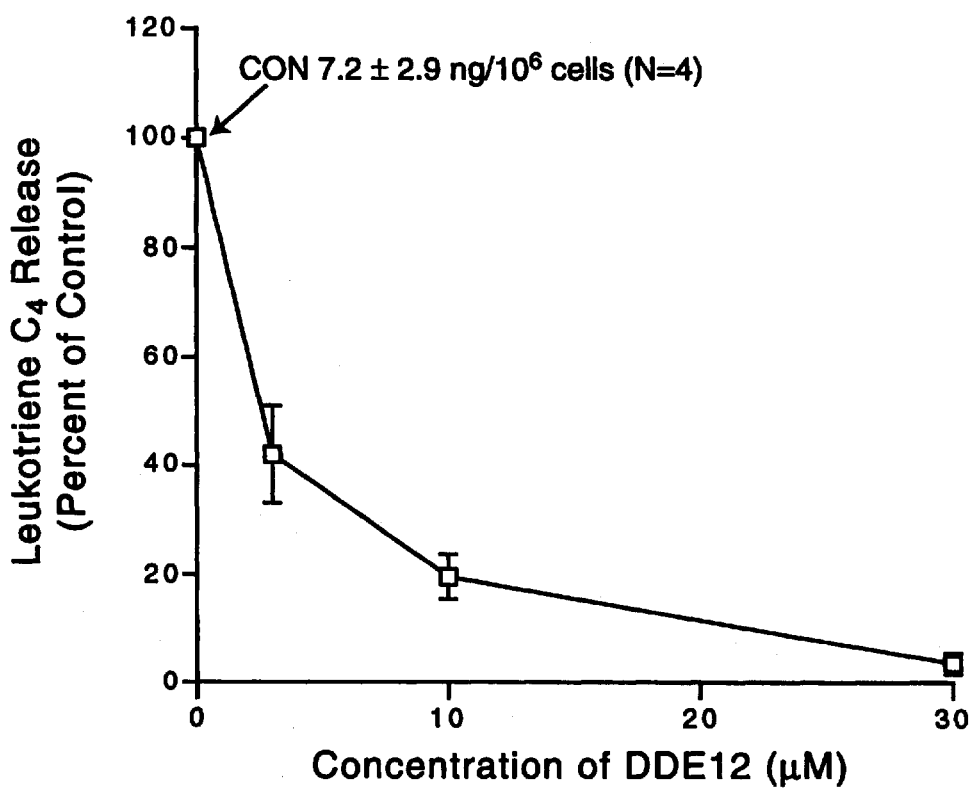
FIG. 2B is a graph showing leukotriene $C_4$ released from RBL-2H3 mast cells incubated with HI-D12.

RBL-2H3 mast cells were preincubated with increasing concentrations of compound HI-D12 or vehicle for 1 hour before challenge with antigen (DNP-BSA). Stimulation of RBL-2H3 mast cells using IgE/antigen resulted in release of significant amounts of β-hexosaminidase (48.5±4.0% of total cellular content, N=4) and LTC$_4$ (7.2±2.9 pg/10$^6$ cells, N=4). Notably, compound HI-D12 inhibited the release of the newly synthesized arachidonic acid metabolite LTC$_4$ in a concentration-dependent fashion (FIG. 2B) but it did not prevent the release of preformed granule-associated β-hexosaminidase (FIG. 2A).

Example 4

Effects of Calanolides on in vivo Mast Cell Responses

Anaphylaxis Model

In order to examine the effect of HI-D12 on passive cutaneous anaphylaxis in mice, dorsal sides of the ears of BALB/c mice were injected intradermally with 20 ng of DNP-IgE (left ears) or PBS (right ears) in 20 μL volume using a 30-gauge needle, as previously described (Miyajima et. al., 1997, J. Clin. Invest. 99:901–914). After 20 hours, mice were treated with compound HI-D12 (15 or 50 mg/kg i.p.) twice at 1 hour intervals prior to the antigen challenge. Control mice were treated with an equal volume of vehicle. Thirty minutes after the last dose of compound HI-D12 or vehicle, mice were challenged with 100 μg antigen (DNP-BSA) in 200 μl 2% Evans blue dye intravenously. Mice were sacrificed by cervical dislocation 30 minutes after the antigen challenge. For quantitation of Evans blue dye extravasation as a measure of anaphylaxis-associated vascular hyperpermeability, 8 mm skin specimens were removed from the ears of mice, minced in 2 ml formamide and incubated at 80° C. for 2 hours in water bath to extract the dye. The absorbance was read at 590 nm. The data were expressed as plasma exudation indices (i.e., times increase in optical density over PBS treated ears at 620 nm).

Results

Figure 3:
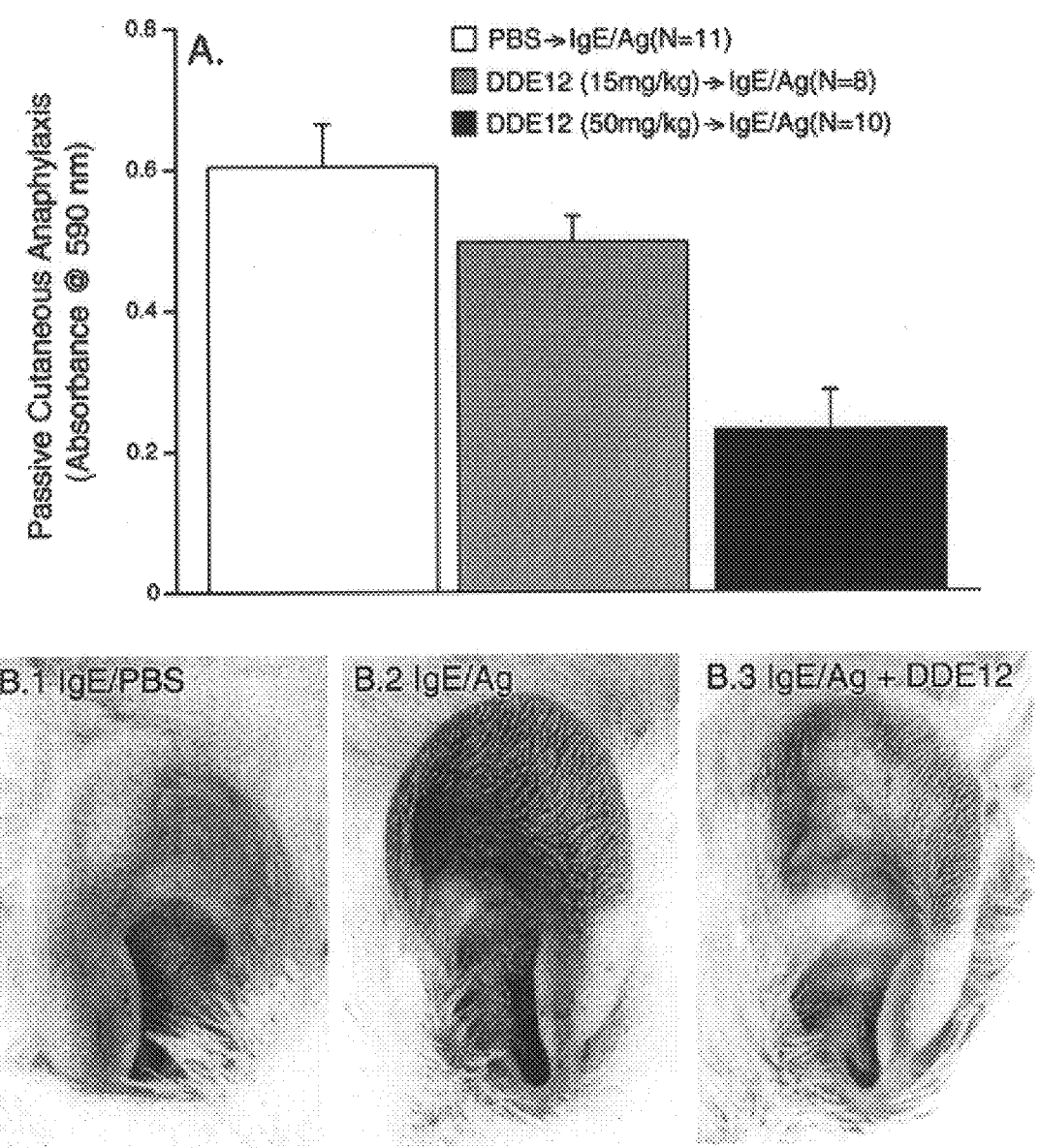
FIG. 3 is a graph showing inhibition of passive cutaneous anaphylaxis in mice treated with the calanolide, HI-D12.

Increased vascular permeability induced by mast cell mediators, such as leukotrienes, is a hallmark of anaphylaxis. The effect of compound HI-D12 on vascular permeability in a well-characterized murine model of passive cutaneous anaphylaxis was examined (Miyajima et. al., 1997 Supra). Compound HI-D12 substantially inhibited the IgE/antigen induced plasma exudation, as measured by extravasation of systemically administered Evan's blue dye, in mice that had been presensitized with antigen specific IgE by 70% at the 50 mg/kg nontoxic dose level (FIG. 3). These results demonstrate that compound HI-D12 is capable of preventing passive cutaneous anaphylaxis by blocking mast cell mediator release in vivo.

Example 5

Homology Model for the Kinase Domain of BTK

The compounds of the invention are designed to fit a composite binding pocket model of the BTK domain. The following describes the construction of the homology model, the modeling of the BTK/calanolide compound complexes using a docking procedure, and structure/function relationships of the lead compound HI-D12 with the binding pocket.

Construction of the Homology Model

A homology model of BTK was constructed using crystal structures of homologous kinase domains of protein kinases HCK, FGFR, IRK, and cAPK (Sicheri et al., 1997, Nature 385:602–9; Mohammadi et al., 1997, Science 276:955–60; Hubbard, 1997, The E. M. O. B Journal 16:5572–5581; and Zheng et al., 1993, Acta Cryst. D49:362–365). The homology modeling of BTK was carried out by first obtaining the protein sequence of BTK (Swiss-Prot # Q06187, Univ. of Geneva, Geneva, Switzerland) from GenBank (National Center for Biotechnology Information, Bethesda, Md.). Next, the most reasonable sequence alignment between the BTK kinase and a coordinate template was determined. This was done by first superimposing the CI coordinates of the kinase domains of HCK, FGFR, IRK, and cAPK using the InsightII program (1996, Molecular Simulations, Inc., San Diego, Calif.) to provide the best overall structural comparison. All four sequences were then aligned based on the superimposition of their structures (amino acid sequences were aligned together if their CI positions were spatially related to each other).

The sequence alignment accommodated such features as loops in a protein which differed from the other protein sequences. The structural superimposition was done using the Homology module of InsightII program and a Silicon Graphics INDIGO2 computer (Silicon Graphics Inc., Mountain View, Calif.). The sequence alignment was manually adjusted based on the previously mentioned considerations, and produced a sequence variation profile for each superimposed CI position.

The sequence variation profile served as a basis for the next procedure, which was sequence alignment of all four proteins with BTK kinase. In this procedure, the sequence of BTK kinase was read into the program and manually aligned with the four known kinase proteins based on the sequence variation profile described previously. Next a set of 3D coordinates was assigned to the BTK kinase sequence using the 3D coordinates of HCK as a template, which employed the Homology module within the InsightII program. The coordinates for a loop region where a sequence insertion occurs (relative to HCK without the loop) was chosen from a limited number of possibilities automatically generated by the program and manually adjusted to a more ideal geometry using the program CHAIN (Sack, J. S. 1988 J. Mol. Graphics 6:244–245). Finally, the constructed model of BTK was subjected to energy minimization using the X-plor program (Brunger, A. T. 1992, New Haven, Conn.) so that any steric strain introduced during the model-building process could be relieved. The model was screened for unfavorable steric contacts and if necessary such side chains were remodeled either by using a rotamer library database or by manually rotating the respective side chains.

The final homology model of the BTK kinase domain had an RMS deviation of 0.01 Å from ideal bond lengths and 2.2° from ideal bond angles after energy minimization. The homology model of BTK was then used, in conjunction with model coordinates of Calanolide and Calanolide derivatives (which were also compared with small molecule crystal structures), for modeling studies of the BTK/inhibitor complexes.

The modeled BTK kinase domain has the expected protein kinase fold with the catalytic site in the center dividing the kinase domain into two lobes. It is composed of a smaller N-terminal lobe connected by a flexible hinge to a larger C-terminal lobe. The N-terminal lobe is rich in β-strands, while the C-terminal region is mostly helical. The catalytic site is defined by two β-sheets that form an interface at the cleft between the two lobes. It is in this catalytic region where small molecule inhibitors can bind. Our modeling studies revealed that the catalytic site of the BTK kinase domain is composed of a distinct planar rectangular binding pocket near the hinge region. The rectangular binding region is defined by residues $Leu^{460}$, $Tyr^{476}$, $Arg^{525}$ and $Asp^{539}$ which occupy the corners of the rectangle. The dimensions of this rectangle are approximately 18 Å×8 Å×9 Å×17 Å and the thickness of the pocket is approximately 7 Å. The far left corner of the rectangle can be visualized as beginning close to the hinge region at $Leu^{460}$ and extending 8 Å towards the upper right to $Asp^{539}$. This is the shortest side of the binding pocket and is located closer to the inner core of the protein. The left side of the pocket, which is the longest, extends from $Leu^{460}$ and traces 18 Å along the hinge region up to $Tyr^{476}$. The right side of the rectangular pocket, opposite to the hinge region, extends about 9 Å from $Asp^{539}$ to $Arg^{525}$, which is immediately adjacent to the binding subsites for the sugar and triphosphate groups of ATP. The hinge region of the binding site is composed of residues 472 to 481. The solvent exposed or fourth side of the rectangle extends 17 Å along the slot-shaped opening to the catalytic site from $Tyr^{476}$ to $Arg^{525}$. The binding pocket is wider at the solvent accessible region, it narrows towards the innermost region of the binding site, and overall it is relatively shallow with a thickness of about 7 Å. The volume of the pocket is approximately 585 Å$^3$.

While most of the catalytic site residues of the BTK kinase domain were conserved relative to other tyrosine kinases, a few specific variations were observed. Residues $Asn^{526}$ and $Asp^{539}$ (opposite the hinge) are conserved in EGFR, IRK, HCK, and BTK. Residue $Thr^{474}$ in the hinge region changes to Met in IRK, JAK1 and JAK3 and residue $Tyr^{476}$ in the hinge region changes to Leu in EGFR and IRK. Residue $Ser^{538}$ of BTK is not conserved in other kinases, but changes to Gly in JAK1 and IRK, to Thr in EGFR, and to Ala in FGF-Receptor, JAK3, and HCK. One region of the binding site contains $Cys^{481}$ in BTK which is more hydrophobic than the corresponding residue of PDGF-Receptor (Asp), FGF-Receptor (Asn), and IRK (Asp). These residue identity differences provide a basis for designing selective inhibitors of the BTK kinase domain.

Docking Procedure Using Homology Model of BTK Kinase Domain

Modeling of the BTK/calanolide and calanolide analog complexes was done using the Docking module within the program insightII and using the Affinity suite of programs for automatically docking a ligand to the receptor. Energy-minimized coordinates for each calanolide or calanolide analog molecule were generated and interactively docked into the ATP binding site of BTK based on the position of quercetin in the HCK/quercetin crystal structure (Sicheri et al., 1997 Nature 385:602–9). The hydrogen atoms on the kinase domain of BTK were generated and potentials were assigned to both receptor and ligand prior to the start of the docking procedure.

The docking method in the InsightII program used the CVFF force field and a Monte Carlo search strategy to search for and evaluate docked structures. While the coordinates for the bulk of the receptor were kept fixed, a defined region of the binding site was allowed to relax, thereby allowing the protein to adjust to the binding of different inhibitors. A binding set was defined within a distance of 5 Å from the inhibitor, allowing residues within this distance to shift and/or rotate to energetically favorable positions to accommodate the ligand.

An assembly was defined consisting of the receptor and inhibitor molecule and docking was performed using the fixed docking mode. Calculations approximating hydrophobic and hydrophilic interactions were used to determine the ten best docking positions of each calanolide or calanolide derivative in the BTK catalytic site. The various docked positions of each Calanolide derivative was qualitatively evaluated using Ludi (Bohm, 1992, J. Comput. Aided. Mol. Des. 6:593–606; and Bohm, 1994, J. Comput. Aided Mol. Des. 8:243–56) in INSIGHTII which was used to estimate a binding constant ($K_i$) for each compound in order to rank their relative binding capabilities and predicted inhibition of BTK. The $K_i$ trends for the calanolide or calanolide derivatives were compared with the trend of the experimentally determined tyrosine kinase inhibition $IC_{50}$ values for the compounds, in order to elucidate the structure-activity relationships (SAR) determining the potency of the calanolide or calanolide derivatives.

The docking scores and predicted binding characteristics for several calanolides is shown in Table 2.

TABLE 2

Predicted Binding of Calanolides

| Compound | Lipophilic Interation Score[a] | HB[b] | HB Score[c] | $IC_{50}$ BTK ($\mu$M) |
|---|---|---|---|---|
| HI-D12 | 631 | 2 | 170 | 29 |
| HI-D63 | 697 | 1 | 85 | 130 |
| HI-D86 | 717 | 1 | 85 | 110 |

[a]Lipophilic interaction score calculated for inhibitor docked into binding site (Ludi program).
[b]HB = Predicted number of hydrogen bonds between the inhibitor and binding site residures of BIK, based on Ludi program (Insightll, Molecular Simulations, Inc.).
[c]Score for ideal hydrogen bond (DH . . . A angle > 90°, D . . . A distance ≤ 2.5 Å)

Structure/Function Relationships Between HI-D12 and BTK Binding Pocket

Molecular modeling showed that HI-D12 can form favorable interactions with specific amino acid residues in the catalytic site of BTK which can enhance binding. As shown in the structured representation below, specific interactions of HI-D12 include the interaction of the hydrogen bonding group, OH in the $X^1$ position (formula I), with Asp 539 and the interaction between the hydrogen bonding group, =O in the $X^2$ position, with Met 477. The propionyl group of HI-D12 is favored over a substituted pyran ring for steric reasons. A propyl group, is favored over OH or carbonyl group because of its polarity.

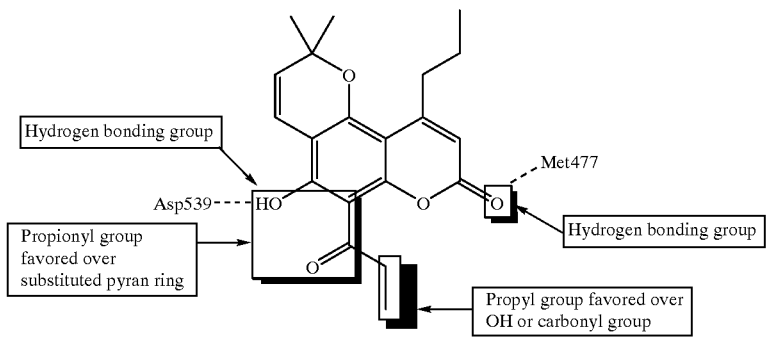

All publications, patents, and patent documents cited are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A method for inhibiting the activity of Tec family tyrosine kinase, comprising contacting the kinase with a compound of formula (I):

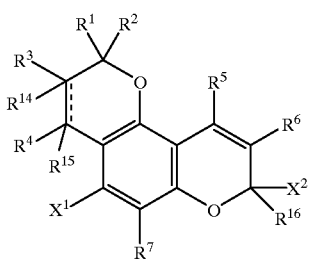

where:

$R^7$ is —C(=O)$R^8$, —CH(—OH)—$R^8$, or —CH$_2$—$R^8$ wherein $R^8$ is ($C_1$–$C_4$) alkyl, or $R^7$ and $X^1$ together form a fused pyran ring;

$R^1$, $R^2$, $R^3$, $R^4$, $R^5$, $R^6$, $R^{14}$, $R^{15}$ and $R^{16}$ are the same or different, and are each independently H, OH, SH, CN, halogen, ($C_1$–$C_4$) alkoxy, ($C_1$–$C_4$) alkylthio, ($C_1$–$C_4$) alkyl, ($C_3$–$C_7$) cycloalkyl, aryl, heteroaryl, or NR$_a$R$^b$; wherein R$^a$ and R$^b$ are each independently hydrogen, ($C_1$–$C_4$) alkyl, ($C_3$–$C_7$) cycloalkyl, aryl, or heteroaryl; or R$^a$ and R$^b$ together with the nitrogen to which they are attached form a ring selected from pyrrolidino, morpholino, and thiomorpholino;

— — — is an optional bond;

$X^1$ is a hydrogen bonding group; and $X^2$ is a hydrogen bonding group, with the proviso that when $R^{16}$ is absent, $X^2$ is a hydrogen bonding group that is doubly bonded to a ring carbon;

or a pharmaceutically acceptable salt thereof.

2. The method of claim 1, wherein:

$X^1$ is OH, SH, NH$_2$, CONH$_2$, or $X^1$ is a ($C_1$–$C_4$) alkyl, ($C_3$–$C_7$) cycloalkyl, aryl, or heteroaryl, each of which is substituted with one or more of OH, SH, NH$_2$, CONH$_2$, COOH; or $X^1$ is O that when taken with $R^7$, forms a fused pyran ring structure; and $X^2$ is =O, =S, =NH, =N—OH, =N—$R^9$, where $R^9$ is ($C_1$–$C_4$) alkyl or ($C_3$–$C_7$) cycloalkyl; or $X^2$ is ($C_1$–$C_4$) alkyl, ($C_3$–$C_7$) cycloalkyl, aryl, or heteroaryl, each of which is substituted with one or more of =O, =S, =NH, =N—OH, =N—OR$^9$, where $R^9$ is ($C_1$–$C_4$) alkyl or ($C_3$–$C_7$) cycloalkyl.

3. (Amended) The method of claim 1, wherein the compound is of the formula (II):

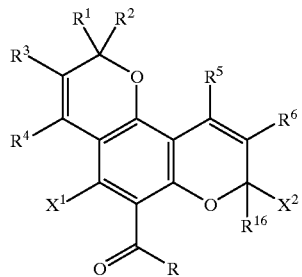

where:

R is ($C_1$–$C_4$)alkyl;

$R^1$, $R^2$, $R^3$, $R^4$, $R^5$, $R^6$ and $R^{16}$ are the same or different, and are each independently H, OH, SH, CN, halogen, ($C_1$–$C_4$) alkoxy, ($C_1$–$C_4$) alkylthio, ($C_1$–$C_6$) alkyl, ($C_3$–$C_7$)cycloalkyl, aryl, heteroaryl, or NR$^a$R$^b$; wherein R$^a$ and R$^b$ are each independently hydrogen, ($C_1$–$C_4$) alkyl, ($C_3$–$C_7$) cycloalkyl, aryl, or heteroaryl; or R$^a$ and R$^b$ together with the nitrogen to which they are attached form a ring selected from pyrrolidino, piperidino, morpholino, and thiomorpholino;

$X^1$ is OH, SH, NH$_2$, CONH$_2$, COOH; or $X^1$ is ($C_1$–$C_4$) alkyl, ($C_3$–$C_7$) cycloalkyl, aryl, or heteroaryl, each of which is substituted with one or more of OH, SH, NH$_2$, CONH$_2$, COOH;

$X^2$ is =O, =S, =NH, =N—OH, =N—OR$_9$, where $R^9$ is ($C_1$–$C_4$) alkyl, or ($C_3$–$C_7$) cycloalkyl; or $X^2$ is ($C_1$–$C_4$) alkyl, ($C_3$–$C_7$) cycloalkyl, aryl, or heteroaryl, each of which is substituted with one or more of =O, =S, =NH, =N—OH, =N—OR$^9$, where $R^9$ is ($C_1$–$C_4$) alkyl or ($C_3$–$C_7$) cycloalkyl;

or a pharmaceutically acceptable salt thereof.

4. The method of claim 1, wherein the compound is of the formula (III):

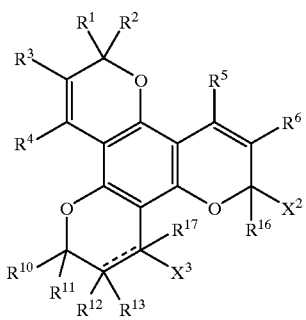

where:

$R^1$, $R^2$, $R^3$, $R^4$, $R^5$ and $R^6$ are the same or different, and are each independently H, OH, SH, CN, halogen, ($C_1$–$C_4$) alkoxy, ($C_1$–$C_4$) alkylthio, ($C_1$–$C_4$) alkyl, ($C_3$–$C_7$) cycloalkyl, aryl, heteroaryl, or NR$^a$R$^b$; wherein R$^a$ and R$^b$ are each independently hydrogen, ($C_1$–$C_4$) alkyl, ($C_3$–$C_7$) cycloalkyl, aryl, or heteroaryl; or R$^a$ and R$^b$ together with the nitrogen to which they are attached form a ring selected from pyrrolidino, piperidino, morpholino, and thiomorpholino;

$R^{10}$, $R^{11}$, $R^{12}$, $R^{13}$, $R^{16}$, and $R^{17}$ are the same or different, and are each independently H, OH, SH, halogen, ($C_1$–$C_4$) alkoxy, ($C_1$–$C_4$) alkylthio, ($C_1$–$C_4$)alkyl, ($C_3$–$C_7$) cycloalkyl, aryl, heteroaryl or $NR^aR^b$; wherein $R^a$ and $R^b$ are each independently hydrogen, ($C_1$–$C_4$) alkyl, ($C_3$–$C_7$) cycloalkyl, aryl or heteroaryl; or $R^a$ and $R^b$ together with the nitrogen to which they are attached form a ring selected from pyrrolidino, piperidino, morpholino, and thiomorpholino;

— — — is an optional bond;

$X^3$ is =O, =S, =NH, =N—OH, =N—$OR^9$, OH, SH, $NH_2$, $CONH_2$ and COOH; where $R^9$ is ($C_1$–$C_4$) alkyl or ($C_3$–$C_7$) cycloalkyl;

or a pharmaceutically acceptable salt thereof.

5. The method of claim 3, where $X^1$ is selected from OH, SH, and $NH_2$.

6. The method of claim 5, where $X^1$ is OH.

7. The method of claim 3, where $X^2$ is selected from =O, =S, and =NH.

8. The method of claim 7, where $X^2$ is =O.

9. The method of claim 4, where $X^3$ is selected from OH and =O.

10. The method of claim 1, wherein the compound has a molecular volume in the range of about 350 Å$^3$ to about 580 Å$^3$.

11. A method of claim 1, wherein the compound is selected from V, and VI, having structural formula:

(IV)
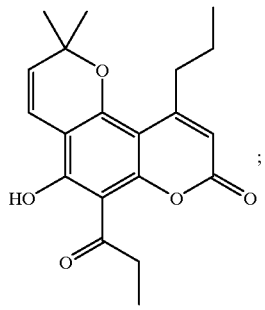

(V)
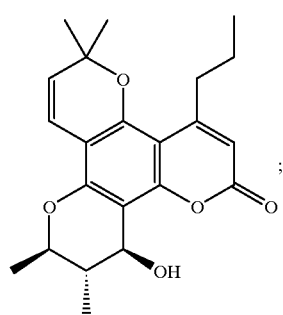

and

-continued (VI)
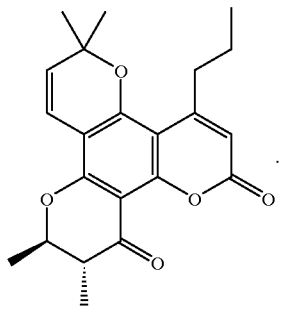

12. The method of claim 1, wherein said contacting comprises binding of the compound to a Tec family kinase catalytic site.

13. A pharmaceutical composition for inhibiting the activity of Tec family tyrosine kinase, comprising an effective amount of a compound of formula I:

(I)

where:

$R^7$ is —C(=O)$R^8$, —CH(—OH)—$R^8$, or —$CH_2$—$R^8$ wherein $R^8$ is ($C_1$–$C_4$) alkyl, or $R^7$ and $X^1$ together form a fused pyran ring;

$R^1$, $R^2$, $R^3$, $R^4$, $R^5$, $R^6$, $R^{14}$, $R^{15}$ and $R^{16}$ are the same or different, and are each independently H, OH, SH, CN, halogen, ($C_1$–$C_4$) alkoxy, ($C_1$–$C_4$) alkylthio, ($C_1$–$C_4$) alkyl, ($C_3$–$C_7$) cycloalkyl, aryl, heteroaryl, or $NR^aR_b$; wherein $R^a$ and $R^b$ are each independently hydrogen, ($C_1$–$C_4$) alkyl, ($C_3$–$C_7$) cycloalkyl, aryl, or heteroaryl; or $R^a$ and $R^b$ together with the nitrogen to which they are attached form a ring selected from pyrrolidino, piperidino, morpholino, and thiomorpholino;

— — — is an optional bond;

$X^1$ is a hydrogen bonding group; and $X^2$ is a hydrogen bonding group, with the proviso that when $R^{16}$ is absent, $x^2$ is a hydrogen bonding group that is doubly bonded to a ring carbon;

or a pharmaceutically acceptable salt thereof, and a pharmaceutically acceptable vehicle.

14. A pharmaceutical composition comprising a therapeutically effective amount of a compound of formula II:

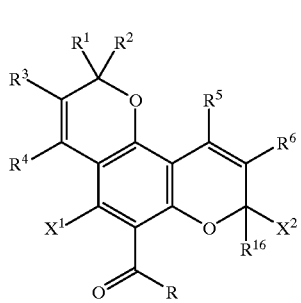

(II)

where:

R is $(C_1-C_4)$ alkyl;

$R^1$, $R^2$, $R^3$, $R^4$, $R^5$, $R^6$, and $R^{16}$ are the same or different, and are each independently H, OH, SH, CN, halogen, $(C_1-C_4)$ alkoxy, $(C_1-C_4)$ alkylthio, $(C_1-C_4)$ alkyl, $(C_3-C_7)$ cycloalkyl, aryl, heteroaryl, or $NR^aR^b$; wherein $R^a$ and $R^b$ are each independently hydrogen, $(C_1-C_4)$ alkyl, $(C_3-C_7)$ cycloalkyl, aryl, or heteroaryl; or $R^a$ and $R^b$ together with the nitrogen to which they are attached form a ring selected from pyrrolidino, piperidino, morpholino, and thiomorpholino;

$X^1$ is OH, SH, $NH_2$, $CONH_2$, COOH; or $X^1$ is $(C_1-C_4)$ alkyl, $(C_3-C_7)$ cycloalkyl, aryl, or heteroaryl, each of which is substituted with one or more of OH, SH, $NH_2$, $CONH_2$, COOH;

$X^2$ is =O, =S, =NH, =N—OH, =N—$OR^9$, where $R^9$ is $(C_1-C_4)$ alkyl, or $(C_3-C_7)$ cycloalkyl; or $X^2$ is $(C_1-C_4)$ alkyl, $(C_3-C_7)$ cycloalkyl, aryl, or heteroaryl, each of which is substituted with one or more of =O, =S, =NH, =N—OH, =N—$OR^9$, where $R^9$ is $(C_1-C_4)$ alkyl or $(C_3-C_7)$ cycloalkyl, with the proviso that when $R^{16}$ is absent, $X^2$ is a hydrogen bonding group that is doubly bonded to a ring carbon;

or a pharmaceutically acceptable salt thereof, and a pharmaceutically acceptable vehicle.

15. The pharmaceutical composition of claim 14, wherein the compound has the structure of formula IV:

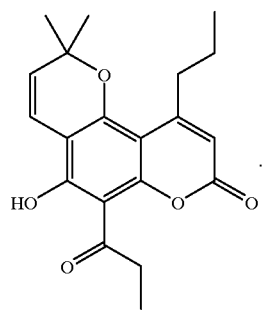

(IV)

16. The pharmaceutical composition of claim 13, wherein the compound has the structure of formula III

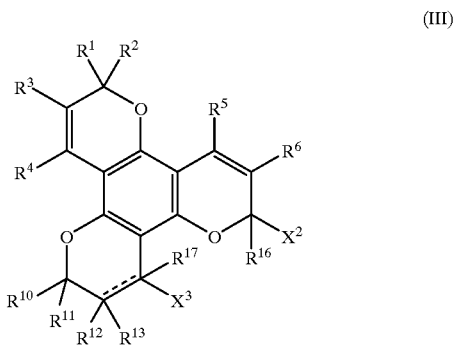

(III)

where:

$R^1$, $R^2$, $R^3$, $R^4$, $R^5$, and $R^6$ are the same or different, and are each independently H, OH, SH, CN, halogen, $(C_1-C_4)$ alkoxy, $(C_1-C_4)$ alkylthio, $(C_1-C_4)$ alkyl, $(C_3-C_7)$ cycloalkyl, aryl, heteroaryl, or $NR^aR^b$; wherein $R^a$ and $R^b$ are each independently hydrogen, $(C_1-C_4)$ alkyl, $(C_3-C_7)$ cycloalkyl, aryl, or heteroaryl; or $R^a$ and $R^b$ together with the nitrogen to which they are attached form a ring selected from pyrrolidino, piperidino, morpholino, and thiomorpholino;

$R^{10}$, $R^{11}$, $R^{12}$, $R^{13}$, $R^{16}$, and $R^{17}$ are the same or different, and are each independently H, OH, SH, CN, halogen, $(C_1-C_4)$ alkoxy, $(C_1-C_4)$ alkylthio, $(C_1-C_4)$ alkyl, $(C_3-C_7)$ cycloalkyl, aryl, heteroaryl or $NR^aR^b$; wherein $R^a$ and $R^b$ are each independently hydrogen, $(C_1-C_4)$ alkyl, $(C_3-C_7)$ cycloalkyl, aryl or heteroaryl; or $R^a$ and $R^b$ together with the nitrogen to which they are attached form a ring selected from pyrrolidino, piperidino, morpholino, and thiomorpholino;

— — — is an optional bond;

$X^3$ is =O, =S, =NH, =N—OH, =N—$OR^9$, OH, SH, $NH_2$, $CONH_2$ and COOH; where $R^9$ is $(C_1-C_4)$ alkyl or $(C_3-C_7)$ cycloalkyl;

or a pharmaceutically acceptable salt thereof.

17. The method of claim 1, wherein said contacting comprises contacting Tec kinase expressing cells.

18. The method of claim 17, wherein said cells are B-cells, mast cells, cancer cells, or platelet cells.

19. The method of claim 1, wherein the Tec family tyrosine kinase is BTK.

20. A method for treating a pathological condition regulated by Tec family tyrosine kinase activity, comprising administering a compound of formula I:

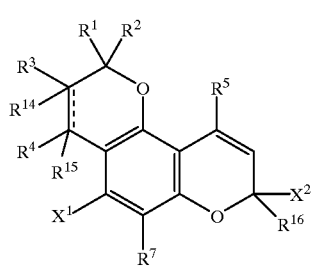

(I)

where:

R$^7$ is —C(=O)R$^8$, —CH(—OH)—R$^8$, or —CH$_2$—R$^8$ wherein R$^8$ is (C$_1$–C$_4$)alkyl, or R$^7$ and X$^1$ together form a fused pyran ring;

R$^1$, R$^2$, R$^3$, R$^4$, R$^5$, R$^6$, R$^{14}$, R$^{15}$, and R$^{16}$ are the same or different, and are each independently H, OH, SH, CN, halogen, (C$_1$–C$_4$) alkoxy, (C$_1$–C$_4$) alkylthio, (C$_1$–C$_4$) alkyl, (C$_3$–C$_7$) cycloalkyl, aryl, heteroaryl, or NR$^a$R$^b$; wherein R$^a$ and R$^b$ are each independently hydrogen, (C$_1$–C$_4$) alkyl, (C$_3$–C$_7$) cycloalkyl, aryl, or heteroaryl; or R$^a$ and R$^b$ together with the nitrogen to which they are attached form a ring selected from pyrrolidino, piperidino, morpholino, and thiomorpholino;

— — — is an optional bond;

X$^1$ is a hydrogen bonding group; and

X$^2$ is a hydrogen bonding group, with the proviso that when R$^{16}$ is absent, X$^2$ is a hydrogen bonding group that is doubly bonded to a ring carbon;

or a pharmaceutically acceptable salt thereof.

21. The method of claim 20, wherein said pathologic condition is cancer.

22. The method of claim 21, wherein said cancer is leukemia, lymphoma, breast cancer, prostate cancer, lung cancer, colon cancer, skin cancer, brain cancer, or bladder cancer.

23. The method of claim 20, wherein the pathologic condition is a B-cell malignancy, a B-cell lymphoproliferative disorder or autoimmune disease, a mast cell disorder, a disease that relates to improper platelet aggregation, or rejection of xenotransplant.

24. The method of claim 20, wherein the pathologic condition is acute lymphoblastic leukemia, chronic lymphocitic leukemia, non-Hodgkin's lymphoma, EBV lymphomia, myeloma, lupus, Crohn's disease, chronic or graft-versus-host disease, allergies, or anaphylactic shock.

25. A method for treating, an allergic reaction comprising administering to a subject a compound of claim 1.

26. A method for inducing expression of genes regulated by BTK comprising administering a compound of claim 1.

27. A method for inducing apoptosis in Tec family tyrosine kinase expressing cells, comprising administering to the cells a compound of claim 1.

28. A method for increasing the sensitivity of cancer cells to chemotherapeutic agents, comprising coadministering a chemotherapeutic agent and a compound of claim 1.

29. A method for inhibiting the activity of BTK in a cell, comprising contacting said cell with the compound of claim 1.

* * * * *